US006713272B2

(12) United States Patent
Anderson et al.

(10) Patent No.: US 6,713,272 B2
(45) Date of Patent: Mar. 30, 2004

(54) ATTACHMENT OF BIOMOLECULES TO HYDROPHOBIC SURFACES

(75) Inventors: George P. Anderson, Lanham, MD (US); J. Matthew Mauro, Silver Spring, MD (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 35 days.

(21) Appl. No.: 09/955,023

(22) Filed: Sep. 19, 2001

(65) Prior Publication Data

US 2003/0054423 A1 Mar. 20, 2003

(51) Int. Cl.⁷ ............................................... G01N 33/53
(52) U.S. Cl. .................... 435/7.92; 435/69.7; 435/7.94; 436/518; 436/523; 436/524; 530/387.3
(58) Field of Search ................... 435/7.1, 7.92, 435/69.1, 69.7, 172.1, 172.3, 328, 287.7; 436/518, 524, 823, 523; 530/387.3

(56) References Cited

U.S. PATENT DOCUMENTS

| | | | |
|---|---|---|---|
| 4,264,766 A | | 4/1981 | Fischer |
| 4,589,881 A | | 5/1986 | Pierschbacher et al. |
| 4,734,362 A | * | 3/1988 | Hung et al. ................. 435/68.1 |
| 4,808,530 A | | 2/1989 | Means et al. |
| 4,931,498 A | | 6/1990 | Pidgeon |
| 5,294,551 A | | 3/1994 | Furcht et al. |
| 5,644,030 A | | 7/1997 | Faulmann |
| 5,747,240 A | * | 5/1998 | Kink et al. ..................... 435/5 |
| 5,811,246 A | | 9/1998 | Anumula et al. |
| 5,853,744 A | | 12/1998 | Mooradian et al. |
| 5,872,094 A | | 2/1999 | Goetinck et al. |
| 6,235,535 B1 | * | 5/2001 | Keinanen et al. ............ 436/172 |
| 6,294,391 B1 | * | 9/2001 | Badley et al. ............... 435/518 |

FOREIGN PATENT DOCUMENTS

| | | | | |
|---|---|---|---|---|
| WO | WO 98/00714 | * | 1/1998 | ......... G01N/33/543 |

OTHER PUBLICATIONS

Sugihara, Seong, Kobatake, Aizawa, Genetically Synthesized Antibody–Binding Protein Self–Assembled on Hydrophobic Matrix, Bioconjugate Chem. 2000, 11, 789–794.

Laukkanen, Teeri, Keinanen, Lipid–Tagged Antibodies: Bacterial Expression and Characterization of a Lipoprotein–Single –Chain Antibody Fusion Protein, Protein Engineering, vol. 6 No. 4, 449–454, 1993.

Vikholm et al, "Layer Formation of a Lipid–Tegged Single–Chain Antibody and the Interaction with Antigen", Elsevier Science S.A., 1996, pp. 924–926.

Vikholm et al, "Incorporation of Lipid–Tagged Single–Chain Antibodies into Lipid Monolayers and the Interaction with Antigen", Langmuir, 1996, vol. 12, No. 13, pp. 3276–3281.

* cited by examiner

*Primary Examiner*—Long V. Le
*Assistant Examiner*—Gary W. Counts
(74) *Attorney, Agent, or Firm*—John J. Karasek; Joseph T. Grunkemeyer

(57) ABSTRACT

A recombinant protein that is a fusion protein containing a protein binding domain and a domain that is post-translationally modified to become lipid-tagged. This molecule has both a domain with highly specific binding capabilities and a domain which is very hydrophobic in nature. This type of molecule can be used to coat hydrophobic surfaces such as polystyrene easily and effectively for use in solid phase binding assays.

12 Claims, No Drawings

ATTACHMENT OF BIOMOLECULES TO HYDROPHOBIC SURFACES

FIELD OF THE INVENTION

The present invention relates to a method for attaching biomolecules to hydrophobic surfaces using a fusion protein which encodes for lipid attachment via post-translational modification.

BACKGROUND OF THE INVENTION

Many routine medical immunoassays are performed on polystyrene or latex surfaces, most commonly involving antibodies immobilized on a carrier such as plastic beads or containers. Conventionally, simple adsorption is the most common method for attaching antibodies to a hydrophobic surface such as a polystyrene container or latex beads. Adsorption is very simple, but it is not always efficient. High concentrations of the protein to be adsorbed are often necessary, and proteins often denature and lose activity when they are adsorbed to a hydrophobic surface. If proteins are adsorbed at a high density, desorption is also a problem, especially if the proteins are exposed to solutions containing detergents.

To overcome the problem with desorption, it is currently necessary to form a covalent attachment of the molecules to the surface. These procedures require a surface with suitable reactive groups available. These groups can be introduced to materials such as polystyrene by very harsh chemical treatment or they can be introduced during the initial manufacture of the material to be coated. Even if the reactive groups exist on the surface, a relatively complex chemistry requiring a heterobifunctional crosslinking reagent is required. This type of crosslinking is generally not orientationally specific, so that often the amount of active material bound to the surface is reduced by 50%.

Huang et al., in *J. Biol. Chem* 255: 8015–8018 (1980), describe coupling fatty acyl groups in lipids to appropriately exposed sulfhydryl and amino acid groups in a protein molecule with a bifunctional reagent. However, in such chemical coupling procedures, the conjugate often forms a heterogeneous complex in terms of number and location of lipid moieties. As a result, this treatment may lead to a loss or decrease in antigen-binding properties.

Other methods have been tried to attach biomolecules such as proteins to substrates, many of which involve using a modified protein as a coating material. For example, Piersbacher et al., in U.S. Pat. No. 4,589,881, disclose polypeptides which have the cell-attachment-promoting activity of fibronectin. These polypeptides are used to prepare a substrate to which cells will attach. In this case the polypeptide is the coating to which biomolecules can be attached.

In another method, Fischer, in U.S. Pat. No. 4,264,766, discloses immunological reagents comprising discrete particles of a latex carrier to which a water-soluble polyhydroxy compound is covalently bound, having condensed thereto a known immunologically active material.

Furcht et al., in U.S. Pat. No. 5,294,551, disclose polypeptides which can bind heparin and promote cellular adhesion and neurite outgrowth. Substrates are coated with these polypeptides in order to culture or grow cells.

Means et al., in U.S. Pat. No. 4,808,530, disclose immobilizing biologically active proteins by reacting the protein with an imidoester or imidothioester having a hydrophobic moiety to form a hydrophobic amidine derivative of the protein, and then adsorbing the protein derivative to a hydrophobic surface.

Anumula et al., in U.S. Pat. No. 5,811,246, disclose a process for immobilizing a compound onto the surface of ELISA plates. The compound is in the form of a compound carrier complex with either avidin-biotin or streptavidin-biotin.

Mootadian et al., in U.S. Pat. No. 5,853,744, disclose a method of covalently attaching a biomolecule to a support by covalently attaching a biomolecule to a support material, attaching a photoreactive crosslinking agent to the immobilized biomolecule to form an immobilized photoreactive analog of the biomolecule, removing the photoreactive analog of the biomolecule from the support material, and attaching the photoreactive analog of the biomolecule to a substrate surface.

Goetnick et al., in U.S. Pat. No. 5,872,094, disclose attaching cartilaginous tissue or protein to a surface by administering a polypeptide capable of promoting the binding of a complex of a proteoglycan and hyaluronic acid to collagen. The administered polypeptide is a fusion polypeptide containing a fragment of cartilage matrix protein and a fragment of link protein. In this case the protein is administered to a patient to repair diseased or injured tissue by promoting the binding of a complex of proteoglycan and hyaluronic acid to collagen.

Takkinen et al., in *Protein Engineering* 4:837–841 (1991) disclose preparing an active single-chain antibody containing a cellulase linker domain which is secreted by *E. coli*. These molecules were designed to allow incorporation of the single chain antibodies into lipid micelles. The lipophilic antibody was genetically engineered and found to be active and capable of functioning in lipid micelles. However, this protein did not provide an enhanced signal over unbound antibody.

SUMMARY OF THE INVENTION

It is an object of the present invention to overcome the aforesaid deficiencies in the prior art.

It is another object of the present invention to provide a simple method for attaching biomolecules to hydrophobic surfaces.

It is a further object of the present invention to provide a simple method for attaching biomolecules to hydrophobic surfaces using a fusion protein which encodes for lipid attachment via post-translational modification.

The present invention involves a recombinant protein that is a fusion protein that contains a bioactive domain such as an immunoglobulin binding domain and a domain that is post-translationally modified to become lipid-tagged. This creates a molecule that has both a domain with highly specific binding capabilities and a domain which is very hydrophobic in nature. Molecules of this type previously were thought to be useful only for preparing lipid micelles or membranes. However, the present inventors have discovered that this type of molecule can be used to coat hydrophobic surfaces such as polystyrene easily and effectively.

The advantage of surface modification by this method is its simplicity. Once the lipid protein is added to the component to be coated, nearly instantaneously the desired protein is adsorbed to the surface.

DETAILED DESCRIPTION OF THE INVENTION

The present invention teaches how to prepare bioactive surfaces using recombinant proteins which are fusion proteins that contain a bioactive domain, e.g., an immunoglobulin binding domain, and a domain that is post-translationally modified to become lipid-tagged. These molecules are extremely hydrophobic, while retaining their binding properties, which makes them ideal for adsorption to hydrophobic surfaces.

Increasing the amount of lipophilic Protein G mixed with polystyrene beads increases the amount of rabbit ant-goat IgG subsequently bound. In the absence of the lipophilic Protein G, only 30% of the IgG was adsorbed during a one hour incubation. Beads which were first coated with the lipophilic protein G bound 95% of the available antibody during a one hour incubation. In addition, once the protein is adsorbed, it is highly resistant to desorption.

Previously, when simple adsorption of proteins was used to coat a surface such as polystyrene, desorption of the protein was always a problem, particularly so in the presence of detergents. The recombinant lipoproteins of the present invention were found to perform excellently. Even in the presence of high detergent concentration, desorption was markedly reduced.

When the lipoproteins of the present invention are used to coat a hydrophobic surface, the protein easily coats the surface and also provides a directional orientation of the molecules on the surface.

Other lipophilic materials can be used to coat hydrophobic surfaces. Materials such as biotin-DPPC, sold by Pierce to prepare biotin labeled micelles, can also effectively coat hydrophobic surfaces. Thus, to prepare a surface with the desired immunoglobulin or protein, it is necessary to covalently label the protein with biotin. The surface is then treated with avidin, which has four binding sites for biotin. It can be used as a bridge between the biotin on the surface and the biotin covalently attached the the desired protein. However, this procedure requires additional steps to prepare the surface, and it is necessary to label the protein to be immobilized with biotin. The biotin labeling is not location specific, so the final surface will not be directionally oriented.

The various methods used in preparing the plasmids and transforming host organisms are well known in the art. These procedures are all described in Maniatis et al., *Molecular Cloning: A Laboratory Manual*, Cold spring Harbor Laboratory, New York, 1982. That is, it is within the skill of those in the genetic engineering art to extract DNA from microbial cells, perform restriction enzyme digestion, electrophorese DNA fragments, anneal plasmid and insert DNA, ligate DNA, transform cells, e.g., *E. coli* cells, prepare plasmid DNA, electrophorese proteins, and sequence DNA.

Bachmair et al., in U.S. Pat. Nos. 5,646,017; 5,496,721; 5,196,321; 5,132,213; and 5,093,242, the entire contents of which are hereby incorporated by reference, disclose methods for designing or modifying protein structure at the protein or genetic level to produce proteins having specified amino-termini, in vivo or in vitro. These methods can be used to produce proteins having amino-termini on biomolecules wherein genes encoding the biomolecules can be made to encode an amino acid of the desired class at the amino-terminus so that the expressed biomolecule exhibits a predetermined amino-terminal structure which renders the biomolecule hydrophobic so that the biomolecule readily adheres to a hydrophobic surface such as polystyrene.

According to the present invention, A DNA sequence containing nucleotides coding for the biomolecule of interest, as well as nucleotides which code for a hydrophobic moiety at the N-terminus of the biomolecule are operably linked to a promoter that will permit expression of the biomolecule in the cells of interest for production thereon. This biomolecule cassette is introduced into cells for production of the hydrophobic biomolecule, after which the hydrophobic biomolecules are recovered therefrom by conventional means.

Any conventional method can be used to prepare the hydrophobic biomolecules of the present invention. For example, the technique of Laukkanen et al., *Protein Engineering* 6(4): 449–454, 1993, involves using the flexible interdomain linker region of a fungal cellulase to link together the variable domains of an anti-2-phenyloxazolone IgG1. The resulting single chain antibody is efficiently secreted and released to the culture medium of *E. coli*. The yield of affinity-purified antibody is 1–2 mg/L of culture medium, and its affinity and stability are comparable to those of the corresponding native IgG.

In another method, Kobatake et al., in *Analytical Chemistry* 69:1295–1298, 1997, produced biosynthetically lipid-tagged anti-2-phenyloxazolone single-chain antibody. The major lipoprotein of *E. coli*, which contains a specific lipid modification at its amino terminus to anchor the bacterial membrane, was used to tag single chain antibodies by fusing the genes for a single-chain anti-2-phenyloxazolone antibody and the essential part of the major lipoprotein of *E. coli* required for modification. The lipid-tagged antibody caries a single covalently bound glycerolipid anchor at the amino-terminal cysteinal residue which is separated from the variable region of the immunoglobulin heavy chain by a linker peptide. These antibodies are used for making immunoliposomes for fluoroimmunoassay.

Because of the degeneracy of the genetic code, the amino acid sequences of recombinant proteins, and fragments thereof, of the present invention can be prepared by using a variety of nucleotide sequences. Functionally equivalent nucleotide sequences can be prepared using known synthetic procedures. Accordingly, the present invention includes functionally equivalent nucleotide sequences.

In addition to covering hydrophobic immunoglobulins, the present invention covers proteins or protein fragments having comparable biological activity which have also been genetically engineered to render them hydrophobic.

The term "equivalent" is used herein as denoting a nucleotide sequence or a polypeptide or protein which performs substantially as the nucleotide sequence, polypeptide, or protein identified here to produce molecules with substantially the same antigenic or immunogenic activity in essentially the same kind of hosts. Equivalency of amino acid sequences can be measured in terms of homology and equivalency of function. Within this definition of "equivalents" are subfragments which have equivalent activity.

Immunochemical assays using the recombinant proteins, or fragments thereof, of the present invention are well suited to solid-phase immunoassay. In a solid phase immunoassay, an immunoglobulin binding protein or peptide which has been genetically engineered to be hydrophobic is immobilized onto a solid phase to form an immunoadsorbent surface. The immunoadsorbent is incubated with the sample to be tested. This surface is then incubated with the antibody or other protein to be immobilized. After an appropriate incubation period, the unbound sample is removed, and a labeled anti-target analyte antibody is used to detect target analyte bound to the immunoabsorbent-antibody conjugate.

Because the genetically engineered proteins of the present invention are hydrophobic, they can readily be immobilized on a variety of supports. Various solid supports can be used, such as beads formed of glass, polystyrene, polypropylene, or other materials. Other suitable solid phases include tubes or plates formed from hydrophobic materials.

For any of the assays in which the hydrophobic molecules of the present invention are used, the ultimate bioassay or immunoassay can be accomplished by any one of a number of means which are well known to those skilled in the art. These means include, but are not limited to, radio-labeling, enzyme-tagging, and fluorescent labeling.

In a preferred embodiment, the basic assay is a sandwich immunoassay in which lipoprotein G binds an IgG such as Anti-Ricin (toxin) or Anti-Anthrax (bacteria). This surface is then used to capture the ricin or anthrax. The detection is completed by using another anti-toxin or bacteria antibody tagged as above.

In another embodiment of the invention, a bare optical probe made of, e.g., polystyrene, is coated with recombinant lipoprotein G. The lipid moiety of the recombinant lipoprotein G adsorbs tightly to the hydrophobic surface of the optical probe. The coated probe is then incubated with antibodies, which are held by the protein G domain. These antibodies are available from many commercial sources and are currently used in a variety of diagnostic assays. The antibodies are held primarily via adsorption to the surface of the probe. Unbound antibody is washed away. The probe is then incubated with target analyte, and a fluorescent tagged antibody is added and allowed to bind to the surface. For the biosensor of the present invention, the amount of fluorescently tagged antibody bound is proportional to the fluorescent signal detected, which reflects the amount of target analyte in the sample.

While the example given is of an immunoassay, the method of the present invention is not limited to immunoassay.

Because antibodies are proteins made by animals to protect them from bacteria or viruses, they have a highly specific binding activity, making them ideal for use in diagnostic assays. Many antibodies are commercially available, so that an antibody of interest can be purchased for use in the assay of the present invention.

In addition to coating hydrophobic surfaces with biomolecules, one may coat a medical implant with a specific protein by genetically engineering the protein to adsorb to a hydrophobic surface.

The foregoing description of the specific embodiments will so fully reveal the general nature of the invention that others can, by applying current knowledge, readily modify and/or adapt for various applications such specific embodiments without undue experimentation and without departing from the generic concept. Therefore, any such adaptations and/or modifications should be comprehended within the meaning and range of equivalents of the disclosed embodiments. It is also to be understood that the phraseology or terminology employed herein is for the purpose of description and not of limitation. The means, materials, and steps for carrying out various disclosed functions may take a variety of alternative forms without departing from the invention.

Thus, the expressions "means to . . . " and "means for . . . ", or any method step language, as may be found in the specification above and/or in the claims below, followed by a functional statement, are intended to define and cover whatever structural, physical, chemical, or electrical element or structure, or whatever method step, which may now or in the future exist which carries out the recited functions, whether or not precisely equivalent to the embodiment to embodiments disclosed in the specification above, i.e., other means or steps for carrying out the same function can be used, and it is intended that such expressions be given their broadest interpretation.

What is claimed is:

1. A bioactive surface comprising a solid substrate coated with a recombinant protein comprising a fusion protein containing a protein binding domain and a domain that is post-translationally modified to become lipid-tagged;

wherein the lipid-tagged domain is adsorbed directly to the solid substrate.

2. The bioactive surface according to claim 1, wherein the solid substrate is hydrophobic.

3. The bioactive surface according to claim 1, wherein the recombinant protein contains an immunoglobulin binding domain.

4. A method for solid phase immunoassay comprising the steps of:

providing a solid substrate coated with a recombinant protein comprising a fusion protein containing a protein binding domain and a domain that is post-translationally modified to become lipid-tagged, the lipid-tagged domain being adsorbed directly to the solid substrate;

incubating the substrate with antibodies to a target analyte and removing unbound antibody after said incubation; incubating the substrate with a sample suspected of containing the target analyte;

adding a labeled antibody and allowing said labeled antibody to bind to the substrate; and measuring the amount of the labeled antibody bound to the substrate and correlating the amount of the labeled antibody bound to substrate with the amount of analyte in the sample.

5. The method according to claim 4, wherein the protein binding domain is an immunoglobulin binding domain.

6. The method according to claim 4, wherein the label is a fluorescent label.

7. A method for preparing a bioactive surface comprising coating a solid substrate with at least one recombinant protein comprising a fusion protein that contains a bioactive domain and a domain that is post-translationally modified to become lipid-tagged;

wherein the lipid-tagged domain is adsorbed directly to the substrate.

8. The method according to claim 7, wherein the bioactive domain is an immunoglobulin binding domain.

9. The method according to claim 7, wherein the substrate is polystyrene.

10. The method according to claim 8, wherein the immunoglobulin binding domain is protein G.

11. The bioactive surface according to claim 1, wherein the lipid-tagged domain is specifically bound to the solid substrate.

12. The bioactive surface according to claim 1, wherein the lipid-tagged domain reduces desorption of the recombinant protein in the presence of a detergent, relative to desorption of the fusion protein without the lipid-tagged domain.

* * * * *